United States Patent [19]
Buysch et al.

[11] Patent Number: 6,071,843
[45] Date of Patent: Jun. 6, 2000

[54] PROCESS FOR REACTIVATING CATALYST SYSTEMS CONTAINING A PLATINUM GROUP METAL

[75] Inventors: Hans-Josef Buysch; Carsten Hesse, both of Krefeld; Johann Rechner, Kempen, all of Germany

[73] Assignee: Bayer Aktiengesellschaft, Leverkusen, Germany

[21] Appl. No.: 08/850,331

[22] Filed: May 2, 1997

[30] Foreign Application Priority Data

May 10, 1996 [DE] Germany .................... 196 18 829

[51] Int. Cl.$^7$ .................................................. B01J 20/34
[52] U.S. Cl. ................... 502/27; 502/29; 502/33; 502/25; 502/30; 502/32
[58] Field of Search ................. 502/22, 29, 33, 502/27, 25, 32, 30

[56] References Cited

U.S. PATENT DOCUMENTS

| | | | |
|---|---|---|---|
| 3,488,295 | 1/1970 | Sennewald et al. | ............ 252/413 |
| 3,700,729 | 10/1972 | Fenton | ............ 260/515 |
| 5,035,777 | 7/1991 | Gardner et al. | ............ 204/79 |

FOREIGN PATENT DOCUMENTS 2815512  10/1979  Germany .

*Primary Examiner*—John F. Niebling
*Assistant Examiner*—Alexander G. Ghyka
*Attorney, Agent, or Firm*—Connolly Bove Lodge & Hutz LLP

[57] ABSTRACT

Platinum metal-containing catalyst systems, which comprise at least one platinum metal, a co-catalyst and other salts, and which are used for the production of diaryl carbonates by the oxidative reaction of aromatic hydroxy compounds with carbon monoxide, can be reactivated by treating the deactivated catalyst system in the liquid phase with an oxidising agent, removing the excess oxidising agent, and reacting the reactivated catalyst system with a carboxylate or diketonate.

27 Claims, No Drawings

PROCESS FOR REACTIVATING CATALYST SYSTEMS CONTAINING A PLATINUM GROUP METAL

The present invention relates to a process for reactivating platinum group metal-containing catalyst systems, which comprise at least one platinum group metal, a co-catalyst and other salts, and which are used for the production of diaryl carbonates by the oxidative reaction of aromatic hydroxy compounds with carbon monoxide, which process is characterised in that the deactivated catalyst system is treated with an oxidising agent, the excess oxidising agent is removed, and the reactivated catalyst system is treated with a diketonate.

It is known that diaryl carbonates can be produced by the oxidative reaction of aromatic hydroxy compounds with carbon monoxide in the presence of a noble metal catalyst (DE-OS 28 15 512). Palladium is preferably used as the noble metal. A co-catalyst (e.g. manganese or cobalt salts), a base, a quaternary salt, various quinones or hydroquinones and drying agents may be used in addition. The reaction can be conducted in a solvent, preferably methylene chloride.

When processes of this type are conducted as continuous processes, a reduction in space-time yield is observed which is due to the deactivation of the homogeneous catalyst system. This results in deactivated catalyst constituents being precipitated as powders from the reaction system. These powders exhibit only a slight catalytic activity, or may even no longer exhibit any catalytic activity at all. The literature contains no information on the reactivation of this catalyst system. In order to maintain a high space-time yield, deactivated catalyst constituents have to be removed from the process and replaced by fresh catalyst. Because the noble metal catalyst constitutes a significant cost factor, and losses of noble metal catalyst have to be replaced in a correspondingly cost-intensive manner, the economic viability of a diaryl carbonate production process which employs a homogeneous catalyst system is strongly dependent on the consumption of platinum metal/co-catalyst. The requirement of the process for fresh catalyst could be drastically reduced by the reactivation of deactivated catalyst systems. The object was therefore to find a simple process by which deactivated catalyst systems can be reactivated.

It has now been found that deactivated platinum group metal-containing catalyst systems, which comprise at least one platinum group metal, a co-catalyst and other salts, and which are used for the production of diaryl carbonates by the oxidative reaction of aromatic hydroxy compounds with carbon monoxide, can be reactivated by treatment with an oxidising agent and the subsequent addition of a diketonate. The unconsumed, excess oxidising agent can be recovered and reused.

The present invention accordingly relates to a process for reactivating deactivated catalysts for the oxidative carbonylation of aromatic hydroxy compounds, which comprise a platinum metal and a metal which acts as a co-catalyst, which is characterised in that the deactivated catalysts are treated at 10–400° C. in the liquid phase with 1–10,000 equivalents of oxidising agents per equivalent of the metallic constituents of the catalyst system, the excess oxidising agent is removed, and the oxidised residue which remains is reacted with 0.1–100 parts by weight of a $C_1$–$C_{12}$ carboxylate or a $C_4$–$C_{12}$ diketonate, with respect to 1 part by weight of the oxidised residue.

It is assumed that carboxylates or diketonates which are soluble in phenol are formed in the course of this procedure.

Metals which act as catalysts, and compounds thereof, are those of the platinum metal group, such as Ru, Rh, Pd, Ir or Pt, preferably Pd.

Metals which act as co-catalysts, and compounds thereof, are those of groups III B, IV B, V B, VI B, VII B, VIII B, I B, II B (CAS nomenclature) or a mixture of a plurality thereof, e.g. manganese, copper, cobalt or vanadium, preferably Mn.

The treatment according to the invention of the deactivated catalyst constituents with an oxidising agent is effected at 10 to 350° C., preferably at 20 to 250° C., most preferably at 30 to 200° C.

The oxidising agents which can be used in the process according to the invention are those compounds or elements which under the reaction conditions accept electrons from the deactivated catalyst constituents; thus when acids are used, for example, a proton $H^+$ accepts an electron according to $2H^+ + 2 e^- \rightarrow H_2$.

Examples of oxidising agents such as these are those of the group comprising strong mineral acids, elemental halogens, $O_2$, $O_3$, peroxy- and hydroperoxy compounds, nitrates, permanganates, halogenates and perhalogenates.

For liquid oxidising agents, the ratio of oxidising agent to catalyst residue in the process according to the invention is 10,000:1, preferably 1000:1, most preferably 500:1. Gaseous oxidising agents are added at a rate of 0.01 to 5000, preferably 0.1 to 500, most preferably 1 to 100 normal liters per gram of catalyst residue per hour.

A period from 0.5 to 20 hours, preferably 0.5 to 10 hours, most preferably 1 to 8 hours, is required for this step of the process according to the invention.

Solid oxidising agents (e.g. iodine, $KMnO_4$, $KClO_4$ etc.) are dissolved in one of the solvents cited below.

Liquid oxidising agents (e.g. bromine, $H_2SO_4$, etc.) can be used in their pure state or diluted with a polar solvent (see below).

Gaseous oxidising agents (e.g. $Cl_2$, $O_2$, $O_3$, hydrogen halides, etc.) are used as a solution in one of the solvents cited below or are bubbled through a suspension of the deactivated catalyst in one of the solvents cited below.

In one possible embodiment of the process according to the invention, the catalyst residue is slurried in one of the solvents described below for its treatment with gaseous oxidising agents (e.g. air or chlorine), and the gaseous oxidising agent is passed through the solution. This can be effected at a pressure of 0.8 to 100 bar, preferably 0.9 to 50 bar, most preferably 0.9 to 10 bar. After the reaction the solvent is removed in the known manner, preferably by distillation, wherein the temperature and pressure can be varied within wide limits without the catalyst being damaged.

If liquid oxidising agents are used, treatment of the catalyst residue with oxidising agents can be conducted under an inert gas atmosphere (nitrogen, argon, etc.), in air or under the usual atmosphere for the oxidative carbonylation of organic hydroxy compounds (carbon monoxide/air, carbon monoxide/oxygen), either unpressurised or under pressure. Excess oxidising agent can be removed by distillation, possibly under reduced pressure, or by destruction with a reducing agent, for example.

The preferred oxidising agents are those from the group consisting of strong mineral acids, more preferably from the group consisting of $H_2SO_4$, $HNO_3$ and hydrogen halides, most preferably from the group consisting of hydrogen halides. In particular, the hydrogen halides are used as aqueous hydrohalic acids, at a concentration of 5 to 70% by weight, preferably 10 to 60% by weight, most preferably 15 to 50% by weight of hydrogen halide with respect to the total weight of acid, preferably as aqueous hydrobromic acid.

Polar solvents are used to form the liquid phase.

Suitable polar solvents are those which do not react with the scheduled oxidising agent. Examples of solvents such as these include those of the group consisting of water, $C_1$–$C_4$ carboxylic acids, esters of $C_1$–$C_4$ carboxylic acids which contain a $C_1$–$C_4$ ester group, amides of $C_1$–$C_4$ carboxylic acids which contain an —$NH_2$—, —$NH(C_1$–$C_4$ alkyl) or —$N(C_1$–$C_4$ alkyl)$_2$ group, aliphatic $C_1$–$C_6$ mono-, di- or polyols, (cyclo)aliphatic $C_1$–$C_6$ mono- or diketones and (cyclo)aliphatic or aromatic $C_2$–$C_7$ nitriles, which are used in an amount of 1 to 1000 parts by weight, preferably 2 to 500, most preferably 5 to 250 parts by weight with respect to 1 part by weight of the deactivated catalyst powder used. The substance which is used as the polar solvent is preferably a mixture which contains water, with an $H_2O$ content of 10–99% of the total weight of the mixture, for example comprising acetic acid or propionic acid or water, preferably water.

In the last step of the process according to the invention, the remaining, oxidised residue from the separation of the excess oxidising agent and the polar solvent is reacted with a carboxylate of $C_1$–$C_{12}$ carboxylic acids or with a $C_4$–$C_{12}$ diketonate, preferably with an acetate or an acetylacetonate. Examples of suitable carboxylates include formates, acetates, propionates, butyrates, pentanoates, hexanoates or caproates which contain cations from the group comprising Li, Na, K, Mg, Ca, Mn, Fe, Co, Ce and the platinum group metal which is contained in the catalyst to be reactivated, such as sodium formate, NaOAc, (where OAc=acetate), KOAc, sodium propionate, sodium butyrate, sodium pentanoate, sodium hexanoate or sodium caproate, alkaline earth metal carboxylates such as $Mg(OAc)_2$ or $Ca(OAc)_2$ or transition metal carboxylates such as $Mn(OAc)_3$, $Mn(OAc)_2$, $Fe(OAc)_2$, $Co(OAc)_2$, $Ce(OAc)_3$ or $Pd(OAc)_2$. Suitable diketonates are those which contain the said cations, and examples thereof include alkali metal acetylacetonates such as Li(acac), where acac=acetylacetonate, Na(acac), K(acac), Rb(acac) and Cs(acac), alkaline earth metal acetylacetonates such as $Mg(acac)_2$ or $Ca(acac)_2$, or transition metal acetylacetonates such as $Cr(acac)_3$, $Mn(acac)_2$, $Mn(acac)_3$, $Fe(acac)_2$, $Fe(acac)_3$, $Co(acac)_2$, $Co(acac)_3$ $Ce(acac)_3$ or $Pd(acac)_2$.

In the process according to the invention, the amount of carboxylate or diketonate which is added is 0.1 to 100, preferably 0.2 to 50, most preferably 0.5 to 25 parts by weight per part by weight of the oxidised catalyst residue after separation of the oxidising agent.

The catalyst which is reactivated by the process according to the invention has an activity which is more than 95% of that of the fresh catalyst.

The following examples serve to explain the process according to the invention, without the process being restricted thereto.

EXAMPLE 1

Reactivation:

2 g of a deactivated catalyst powders (content determined by absorption spectroscopy: 33.9% palladium, 14.5% manganese, balance up to 100%: $Na^+$ and $Br^-$ ions), which originated from a previous semi-batch lot for the production of diphenyl carbonate (DPC; 10 bar reaction pressure, 65 ppm Pd, about 500 ppm Mn), were treated with 50 ml of a 48% by weight aqueous solution of hydrogen bromide and heated to 100° C. A homogeneous solution was obtained after one hour. The HBr solution was then distilled off at a pressure of 30 mbar and at a temperature of 80° C. in a rotary evaporator. The proportion of HBr recovered was 98%. The residue was dried in air and weighed 3.22 g (weight increase due to Br uptake). The HBr recovered by means of the rotary evaporator could be re-used directly.

Reuse in catalysis:

0.65 g of the reactivated catalyst (=136 mg palladium and 58 mg manganese) and 8.31 g tetrabutylammonium bromide were dissolved at 80° C. in 450 g phenol in an autoclave (1 liter) fitted with a sparging stirrer, a condenser and a downstream cold trap. 0.51 g manganese(II) acetylacetonate and 2.21 g sodium phenolate, dissolved in 50 g phenol, were then added, and the pressure was set to 10 bar whilst passing in a gas mixture comprising carbon monoxide and oxygen (96.5:3.5 vol. %). The manganese content of the reaction solution was 330 ppm. The amount of gas mixture was adjusted to 260 Nl/hour. A sample was taken once an hour from the gas mixture and was analysed by gas chromatography.

The analyses showed that the reaction mixture contained 7.4% diphenyl carbonate after one hour, 12.2% diphenyl carbonate after 2 hours and 17.4% diphenyl carbonate after 3 hours; this corresponded to a mean activity of 98.0% of the fresh catalyst which was used at first.

Comparative test with fresh catalyst:

0.34 g palladium bromide (=136 mg palladium) and 8.31 g tetrabutylammonium bromide were dissolved at 80° C. in 450 g phenol in an autoclave (1 liter) fitted with a sparging stirrer, a condenser and a downstream cold trap. Carbon monoxide (3 liter/hour) was passed through this solution for one hour in order to activate the catalyst. 0.77 g manganese (II) acetylacetonate and 2.21 g sodium phenolate, dissolved in 50 g phenol, were then added, and the pressure was set to 10 bar whilst passing in a gas mixture comprising carbon monoxide and oxygen (96.5:3.5 vol. %). The manganese content of the reaction solution was 330 ppm. The amount of gas mixture was adjusted to 260 Nl/hour. A sample was taken once an hour from the gas mixture and was analysed by gas chromatography.

The analyses showed that the reaction mixture contained 7.6% diphenyl carbonate after one hour, 12.4% diphenyl carbonate after 2 hours and 17.7% diphenyl carbonate after 3 hours.

EXAMPLE 2

The procedure was as in Example 1, except that the deactivated catalyst powder was not treated with 48% by weight aqueous hydrogen bromide solution, but was treated instead with 98% sulphuric acid. A homogenous solution was obtained after one hour at 100° C. 95% of the sulphuric acid was recovered by distillation under vacuum. The resultant reactivated catalyst exhibited an activity of 96% of that of the fresh catalyst when reused in the process for the oxidative carbonylation of aromatic hydroxy compounds.

EXAMPLE 3

The procedure was as in Example 1, except that the deactivated catalyst powder was not treated with 48% by weight aqueous hydrogen bromide solution, but was treated instead with 65% nitric acid. A homogenous solution was obtained after one hour at 80° C. 99% of the nitric acid was recovered by distillation under vacuum. The resultant reactivated catalyst exhibited an activity of 98% of that of the fresh catalyst when reused in the process for the oxidative carbonylation of aromatic hydroxy compounds.

EXAMPLE 4

The procedure was as in Example 1, except that the deactivated catalyst powder was not treated with 48% by weight aqueous hydrogen bromide solution, but was treated instead with 24% aqueous hydrobromic acid. A homogenous solution was obtained after one hour at 100° C. 98% of the hydrobromic acid was recovered by distillation under vacuum. The resultant reactivated catalyst exhibited a mean activity of 98% of that of the fresh catalyst when reused in the process for the oxidative carbonylation of aromatic hydroxy compounds.

EXAMPLE 5

The procedure was as in Example 1, except that 1.9 g (=15.5 mmole) of sodium acetylacetonate were added to the resulting deactivated catalyst after the recovery of the hydrobromic acid.

Reuse in catalysis:

1.03 g of the reactivated catalyst (=136 mg palladium and 58 mg manganese) and 8.31 g tetrabutylammonium bromide were dissolved at 80° C. in 450 g phenol in an autoclave (1 liter) fitted with a sparging stirrer, a condenser and a downstream cold trap. 0.51 g manganese(II) acetylacetonate and 2.21 g sodium phenolate, dissolved in 50 g phenol, were then added, and the pressure was set to 10 bar whilst passing in a gas mixture comprising carbon monoxide and oxygen (96.5:3.5 vol. %). The manganese content of the reaction solution was 330 ppm. The amount of gas mixture was adjusted to 260 Nl/hour. A sample was taken once an hour from the gas mixture and was analysed by gas chromatography.

The analyses showed that the reaction mixture contained 7.5% diphenyl carbonate after one hour, 12.3% diphenyl carbonate after 2 hours and 17.5% diphenyl carbonate after 3 hours; this corresponded to a mean activity of 98.9% of the fresh catalyst which was used at first.

We claim:

1. A process for reactivating deactivated homogeneous catalysts for the oxidative carbonylation of aromatic hydroxy compounds which comprise a platinum group metal and a metal acting as a co-catalyst, which comprises treating the deactivated catalysts at 10–400° C. in the liquid phase with 1–10,000 equivalents of oxidising agents per equivalent of the metallic constituents of the catalysts, removing excess oxidising agent, and treating the oxidised residue which thereby remains with 0.1–100 parts by weight of a $C_1$–$C_{12}$ carboxylate or a $C_4$–$C_{12}$ diketonate, with respect to 1 part by weight of the oxidised residue.

2. A process according to claim 1, wherein the platinum group metal is palladium.

3. A process according to claim 1, wherein the co-catalyst is selected from the group consisting of III B, IV B, V B, VI B, VII B, VIII B, I B, II B or mixtures thereof.

4. A process according to claim 1, wherein the oxidising agent is selected from the group consisting of strong mineral acids, elemental halogens, $O_2$, $O_3$, peroxy and hydroperoxy compounds, nitrates, permanganates, halogenates, perhalogenates, used in an amount of 1–10,000 equivalents of oxidising agent per equivalent of the metallic constituents of the catalyst to be reactivated.

5. A process according to claim 4, wherein the oxidising agent is a hydrogen halide used in the form of aqueous hydrohalic acids in a concentration of 5–70% by weight of hydrogen halide with respect to the total weight of acid.

6. A process according to claim 1 wherein a polar solvent is present for the oxidising agent and the solvent is one or more of the group consisting of water, $C_1$–$C_4$ carboxylic acids, esters of carboxylic acids which comprise a $C_1$–$C_4$ ester group, amides of $C_1$–$C_4$ carboxylic acids which $C_1$–$C_4$ comprise an —$NH_2$—, —$NH(C_1$–$C_4$ alkyl) or —$N(C_1$–$C_4$ alkyl$)_2$ group, aliphatic $C_1$–$C_6$ mono-, di- or polyols, (cyclo) aliphatic $C_1$–$C_6$ mono- or diketones and (cylco)aliphatic or aromatic $C_2$–$C_7$ nitriles.

7. A process according to claim 6, wherein the polar solvent is a mixture which comprises water.

8. A process according to claim 1, wherein the carboxylates and diketonates are metal salts.

9. A process according to claim 1, wherein 1 to 1000 equivalents of oxidising agent are used per equivalent of the metallic constituents of the catalyst to be reactivated.

10. A process according to claim 1, wherein 0.2 to 50 parts by weight of carboxylate or diketonate are used with respect to 1 part by weight of the oxidised residue.

11. A process according to claim 3, wherein the co-catalyst is Mn.

12. A process according to claim 4, wherein the oxidising agent is a strong mineral acid.

13. A process according to claim 12, wherein the strong mineral acid is $H_2SO_4$ or $HNO_3$.

14. A process according to claim 4, wherein the oxidising agent is a hydrogen halide.

15. A process according to claim 5, wherein the hydrogen halide is aqueous hydrobromic acid.

16. A process according to claim 5, wherein the concentration of hydrogen halide used is 10–60% by weight.

17. A process according to claim 16, wherein the concentration of hydrogen halide is 15–50% by weight.

18. A process according to claim 6, wherein the polar solvent present for the oxidising agent is used in an amount of 1 to 1000 parts by weight with respect to 1 part by weight of the deactivated catalyst powder.

19. A process according to claim 18, wherein the polar solvent is used in an amount of 2 to 500 parts by weight.

20. A process according to claim 19, wherein the polar solvent present for the oxidising agent is used in the amount of 5 to 250 parts by weight.

21. A process according to claim 8, wherein the carboxylates and diketonates are metal salts of metals selected from the group consisting of Li, Na, K, Mg, Ca, Mn, Fe, Co, Ce and the platinum group metal which is contained in the catalyst to be reactivated.

22. A process according to claim 9, wherein 1 to 500 equivalents of oxidising agent are used.

23. A process according to claim 10, wherein 0.5 to 25 parts by weight of carboxylate or diketonate are used.

24. A process for regenerating deactivated, homogenous catalyst systems for the oxidative carbonylation of aromatic hydroxy compounds which catalyst system comprises a platinum group metal, and a co-catalyst metal, which process consists essentially of recovering platinum group metal and co-catalyst metal, treating the catalyst with sulphuric acid, nitric acid or hydrobromic acid until a homogeneous solution is obtained, and removing excess acid.

25. A process according to claim 24, wherein the treatment is carried at 100° C. for 1 hour.

26. A process according to claim 24, wherein the treatment is carried out with hydrobromic acid.

27. A process according to claim 26, wherein the hydrobromic acid is 24–48% by weight hydrobromic acid.

* * * * *